(12) United States Patent
Black et al.

(10) Patent No.: US 7,335,485 B2
(45) Date of Patent: Feb. 26, 2008

(54) DEVICE AND METHOD FOR DETERMINING ANTIBIOTIC SUSCEPTIBILITY

(75) Inventors: Jennifer A. Black, Omaha, NE (US); Ellen S. Moland, Crescent, IA (US); Kenneth Thomson, Omaha, NE (US)

(73) Assignee: Creighton University, Omaha, NE (US)

( * ) Notice: Subject to any disclaimer, the term of this patent is extended or adjusted under 35 U.S.C. 154(b) by 0 days.

(21) Appl. No.: 11/636,103

(22) Filed: Dec. 8, 2006

(65) Prior Publication Data

US 2007/0082376 A1   Apr. 12, 2007

Related U.S. Application Data

(62) Division of application No. 11/177,714, filed on Jul. 8, 2005, now Pat. No. 7,166,442, which is a division of application No. 10/387,788, filed on Mar. 13, 2003, now abandoned.

(60) Provisional application No. 60/364,232, filed on Mar. 13, 2002.

(51) Int. Cl.
*C12Q 1/00* (2006.01)
*C12Q 1/02* (2006.01)
*C12Q 1/18* (2006.01)

(52) U.S. Cl. ............... 435/29; 435/32; 435/34; 435/35

(58) Field of Classification Search ............ 435/29, 435/32, 34, 35
See application file for complete search history.

(56) References Cited

U.S. PATENT DOCUMENTS

| 5,338,664 | A | | 8/1994 | Tuckman et al. |
| 5,466,583 | A | | 11/1995 | Thomson et al. |
| 5,501,959 | A | * | 3/1996 | Lancaster et al. ............ 435/32 |
| 5,747,276 | A | | 5/1998 | Hoch et al. |
| 5,998,159 | A | | 12/1999 | Watson et al. |
| 2004/0005653 | A1 | * | 1/2004 | Chen et al. .................. 435/34 |

OTHER PUBLICATIONS

U.S. Appl. No. 60/347,485.*
Reisbig, MD & Hanson, ND The ACT-1 plasmid-encoded AmpC β-lactamase is inducible: Detection in a complex beta-lactamase background. J Antimicrob Chemother (2002) 49:557-560.
Hanson, ND et al. Molecular characterization of a multiply resistant *Klebsiella pneumoniae* encoding ESBLs and a plasmid-mediated AmpC. J Antimicrob Chemother (1999) 44:377-380.
Pitout, JD et al. Modification of the double-disk test for detection of *Enterobacteriaceae* producing extended-spectrum and AmpC β-lactamases. J Clin Microbiol (2003) 41:3933-3935.
Coudron, PE et al. Occurrence and detection of AmpC beta-lactamases among *Escherichia coli*, *Klebsiella pneumoniae*, and *Proteus mirabilis* isolates at a veterans medical center. J Clin Microbiol (2000) 38:1791-1796.
Yong, D et al. Further modification of the Hodge test to screen AmpC β-lactamase (CMY-1)- producing strains of *Escherichia coli* and *Klebsiella pneumoniae*. J Microbiol Methods (2002) 51:407-410.
Brown DF & Brown L Evaluation of the E test, a novel method of quantifying antimicrobial activity. J Antimicrob Chemother (1991) 27:185-190.
Thomson KS & Sanders CC Detection of extended-spectrum β-lactamases in members of the family *Enterobacteriaceae*: Comparison of the double-disk and three-dimensional tests. Antimicrob Agents Chemother (1992) 36:1877-1882.
Soto, U.L., et al. (1987). Resistance of *Pseudomonas aeruginosa* to β-Lactam Antibiotics, *Folia Microbiol.* 1987, 32, 290-296.
Haque, H.., et al. (1975). Cell Envelopes of Gram negative Bacteria: Composition, Response to Chelating Agents and Susceptibility of Whole Cells to Antibacterial Agents, *J. appl. Bact.* 1976, 40, 89-99.
Nikaido, H., et al. (1985). Molecular Basis of Bacterial Outer Membrane Permeability, *Microbiological Reviews*, Mar. 1985, p. 1-32.
Rasmussen, B., et al. (1997). Carbapenem-Hydrolyzing β-Lactamases, *Antimicrobial Agents and Chemotherapy*, 41(2), 223-232.
Livermore, D. (1997). Acquired carbapenemases, *Journal of Antimicrobial Chemotherapy*, 39, 673-676.

(Continued)

*Primary Examiner*—Ruth A Davis
(74) *Attorney, Agent, or Firm*—Stinson Morrison Hecker LLP

(57) ABSTRACT

The present invention provides a method of determining the antibiotic susceptibility of a microorganism comprising the following steps. First, a culture of the microorganism whose susceptibility is to be determined is admixed with an antibiotic to which susceptibility is to be assayed, and a permeabilizing agent for the microorganism present in a non-growth-inhibiting microorganism-permeabilizing effective amount to form an assay culture. Next, the assay culture is incubated under appropriate culture conditions and for a time sufficient to determine the susceptibility of the microorganism to the antibiotic. In another aspect, the present invention provides an improved method for antibiotic susceptibility testing of a microorganism in a culture by admixing the culture with an antibiotic to which susceptibility is to be assayed, and incubating the culture for a time sufficient to determine the susceptibility of the microorganism to the antibiotic, the improvement comprising admixing the culture with a permeabilizing agent for the microorganism present in a non-growth inhibiting microorganism-permeabilizing effective amount.

40 Claims, 4 Drawing Sheets

OTHER PUBLICATIONS

Hirakata, Y., et al. (1998) Rapid Detection and Evaluation of Clinical Characteristics of Emerging Multiple-Drug-Resistant Gram-Negative Rods Carrying the Metallo-β-Lactamase Gene $bla_{imp}$, *Antimicrobial Agents and Chemotherapy*, 42(8), 2006-2011.

Arakawa, Y., et al. (2000) Convenient Test for Screening Metallo-β-Lactamase-Producing Gram-Negative Bacteria Using Thiol Compounds, *Journal of Clinical Microbiology*, 38(1), 40-43.

Walsh, T., et al. (2002) Evaluation of a New Etest for Detecting Metallo-β-Lactamase in Routine Clinical Testing, *Journal of Clinical Microbiology*, 40(8), 2755-2759.

Yong, D., et al. (2002) Imipenem-EDTA Disk Method for Differentiation of Metallo-β-Lactamase-Producing Clinical Isolates of *Pseudomonas* spp. and *Acinetobacter* spp., *Journal of Clinical Microbiology*, 40(10), 3798-3801.

Walsh, T., et al. (2005). Metallo-β-Lactamases: the Quiet before Storm?, *Clinical Microbiology Reviews*, 18(2), 306-325.

Hong, S., et al. (2006). Tris-EDTA (TE) Disk Test for Detection of Metallo-β-Lactamase (MBLs) in Clinical Isolates. Submitted May 2006 to http://www.icaac.org/.

Moland, E., et al. (2006). U.S. Isolate of *Kiebsiella pneumoniae* (KP) Producing VIM Metallo-β-lactamase (MBL) and SHV-5-like ESBL. Submitted May 2006 to http://www.icaac.org/.

Moland, E., et al. (2006). Simple Disk Test for Detection of Carbapenem Hydrolyzing Enzymes (CHEs). Submitted May 2006 to http://www.icaac.org/.

Hong, S., et al. (2006). Indirect Tris-EDTA (TE) Disk Test for Detection of Class A Carbapenemases in Clinical Isolates. Submitted May 2006 to http://www.icaac.org/.

Kim, S., et al. (2006). Convenient Test Using Combination of Chelating Agents for Detection of Metallo-β-Lactamase in the Clinical Laboratory. Submitted May 2006 to http://www.icaac.org/.

Black, Jennifer A., et al. AmpC Disk Test for Detection of Plasmid-Mediated AmpC β-Lactamases in Enterobacteriaceae Lacking Chromosomal AmpC β-Lactamases. Journal of Clinical Microbiology, Jul. 2005, p. 3110-3113.

\* cited by examiner

DEVICE AND METHOD FOR DETERMINING ANTIBIOTIC SUSCEPTIBILITY

CROSS-REFERENCE TO RELATED APPLICATIONS

The present application is a divisional application of U.S. Divisional application Ser. No. 11/177,714 filed on Jul. 8, 2005 now U.S. Pat. No. 7,166,442 which is a division application of U.S. application Ser. No. 10/387,788, filed Mar. 13, 2003 now abandoned, which claims priority of U.S. Provisional Application Ser. No. 60/364,232, filed Mar. 13, 2002, all of which are incorporated herein by reference in their entirety.

STATEMENT REGARDING FEDERALLY SPONSORED RESEARCH OR DEVELOPMENT

[Not applicable.]

BACKGROUND OF THE INVENTION

Clinicians and veterinarians often select antibiotic therapies for infections on the basis of laboratory test results. The laboratory tests, known as antimicrobial or antibiotic susceptibility tests, determine the inhibitory activity of antibiotics against the microorganisms that cause infections. If the antibiotic susceptibility test indicates that an antibiotic is sufficiently potent to treat an infection, the microorganism causing the infection is reported to be "susceptible" to the antibiotic. If the test indicates a lack of sufficient antimicrobial potency for successful therapy, the microorganism is reported as "resistant" to the antibiotic. In some tests other categories of susceptibility may be reported, e.g. "moderate susceptibility" or "intermediate susceptibility."

A problem with currently available antimicrobial susceptibility tests is their failure to reliably predict the outcome of therapy. Sometimes an antibiotic will fail to cure an infection even though the microorganism is susceptible to the antibiotic in the laboratory test. That is, the current routine laboratory tests can be misleading and give an over-optimistic impression of the therapeutic potential of antibiotics. These tests can therefore cause patients to be given ineffective treatments. In serious infections, this inadequacy of current laboratory tests can have fatal consequences.

There are many reasons for failures of antibiotic therapies that were initiated on the basis of antibiotic susceptibility tests. Some involve patient-related factors. Some involve pathogen-related factors. However one explanation is error arising from a deficiency in the antibiotic susceptibility test itself. That deficiency is that current routine antibiotic susceptibility tests do not detect the antibiotic-inactivating potential of some microorganisms. Some microorganisms produce enzymes that inactivate antibiotics. The best known enzymes of this type are the β-lactamases that certain bacteria produce to inactivate β-lactam antibiotics. Such enzymes, which are not reliably detected in routine antibiotic susceptibility tests, may cause sufficient antibiotic inactivation at the site of an infection in a patient to cause a treatment failure.

Plasmid-mediated AmpC β-lactamases were first reported in the 1980's. Bauernfeind, A., Y. Chong, and S. Schweighart 1989. Extended broad-spectrum β-lactamase in *Klebsiella pneumoniae* including resistance to cephamycins. Infection. 17:316-321. They arose as a consequence of the transfer of chromosomal genes for inducible AmpC β-lactamases onto plasmids. These enzymes have been reported in isolates of *E. coli, K. pneumoniae, K. oxytoca, Salmonella* spp., *Citrobacter freundii, Enterobacter aerogenes*, and *Proteus mirabilis*. The genes are typically encoded on large plasmids containing other antibiotic encoding resistance genes, leaving few therapeutic options. Although it has been over ten years since plasmid-mediated AmpC β-lactamases were discovered, most clinical labs and physicians remain unaware of their clinical importance. As a result, plasmid-mediated AmpC β-lactamases often go undetected. Without detection, correct therapy for infected patients may not be given.

Currently there are no NCCLS recommendations for detection of plasmid-mediated AmpC β-lactamases. The three-dimensional test has been used to detect these enzymes. However, this test is technically demanding and this has precluded its widespread adoption. Multiplex PCR is also currently available as a research tool for detection of plasmid-mediated AmpC β-lactamases, but is not yet available as a routine test for clinical labs. Perez-Perez F J, Hanson N D 2002. Detection of plasmid-mediated AmpC beta-lactamase genes in clinical isolates by using multiplex PCR. J Clin Microbiol. 40(6):2153-62.

The currently used antibiotic susceptibility tests, which measure only the antimicrobial activity of antibiotics and not the ability of the microorganisms to cause antibiotic inactivation, fail to take into account this very important determinant of the outcome of therapy. This deficiency in the tests places clinicians at a disadvantage in selecting the most appropriate antibiotics for their infected patients.

In summary, there is a need for antibiotic susceptibility tests that provide clinicians with information about both the antimicrobial activity of antibiotics and, additionally, the ability of microorganisms to inactivate antibiotics. Such tests should improve the quality of therapeutic decision-making by clinicians when selecting antibiotic therapies for patients with infections.

Antibiotic susceptibilities are determined routinely by either disk diffusion or antibiotic dilution methods, or by methods that are derivatives of these two methods. In disk diffusion methods [for example see Bauer, A. W. et al., American Journal of Clinical Pathology. 45:493-496 (1966); Bell, S. M., Pathology. 7:Suppl 1-48 (1975); Stokes, E. J., et al., Association of Clinical Pathologists Broadsheet, No. 55 (revised) (1972)] a standard quantity of the causative microorganism is uniformly spread over the surface of an appropriate culture medium (hereafter referred to as agar). Then several filter paper disks impregnated with specific amounts of selected antibiotics are placed on the agar surface. The agar is then incubated for an appropriate period at an appropriate temperature. During incubation the antibiotics diffuse out of the disks into the agar and the microorganism grows on the surface of the agar, except in the areas where antibiotics inhibit its growth. Inhibition of growth is detected as clear zones of no growth (inhibition zones) on the agar around the antibiotic disks. The sizes of the inhibition zones are measured and compared to established interpretive criteria to determine the microorganism's susceptibility or resistance to antibiotics.

Dilution methods test antibiotic susceptibility on either solid agar or in liquid broth. [National Committee for Clinical Laboratory Standards 1997. Methods for dilution antimicrobial susceptibility tests for bacteria that grow aerobically. Approved standard M7-A4. National Committee for Clinical Laboratory Standards, Villanova, Pa.] In the dilution method a constant quantity of microbial inoculum is introduced into a series of tubes or wells of broth (or onto one or more agar plates) containing varying concentrations of antibiotic. After incubation for an appropriate period the broth (or agar) tests are inspected and the lowest concentration of antibiotic that prevents detectable growth of the microorganism recorded. This concentration is the minimum inhibitory concentration (MIC) of the antibiotic.

Both disk diffusion and dilution methods are generally deficient in that they do not yield information about the ability of microorganisms to inactivate antibiotics.

Various techniques for detecting antibiotic-inactivating enzymes of bacteria have been reported in the scientific literature. Some techniques are used to detect the activity of specific antibiotic-inactivating enzymes (e.g. β-lactamases), while others are non-specific and detect enzymes that inactivate more than one class of antibiotics. The following are exemplary tests used to detect antibiotic-inactivating enzymes of bacteria.

Specific tests for the detection of chloramphenicol acetyltransferase are reviewed in Chauchereau, A., et al., Analytical Biochemistry. 188:310-316 (1990). These are complex tests to detect enzymatic inactivation of chloramphenicol and require special instruments capable of measuring the absorbance of light at specific wavelengths or of measuring radioactivity. Such tests are not antibiotic susceptibility tests and their complexity is such that they are unsuitable for routine clinical microbiology laboratories.

The production of β-lactamases by *Staphylococcus aureus* is inferred by the production of a distinctive heaped-up margin of the inhibition zone around a penicillin antibiotic disk. Gill, V. J., et al., J. Clin. Microbiol. 14:437-40 (1981). Beta-lactamase production by many types of bacteria can also be detected chemically by testing the bacteria with an indicator substance such as nitrocefin. Oberhofer, T. R., et al., J. Clin. Microbiol. 15:196-9 (1982); O'Callaghan, C. H., et al., A.A.C. 1:283-288 (1972). These tests are reliable indicators only of β-lactamase-determined resistance of *Staphylococcus aureus, Staphylococcus epidermidis, Moraxella catarrhalis, Neisseria* and *Haemophilus* species to certain types of penicillin antibiotics. They do not predict the potential for any other bacteria to resist these penicillins, and they do not predict the potential for any bacteria to be resistant to any of the other classes of β-lactam antibiotics, such as cephalosporins, cephamycins, monobactams, monocarbams, penems or carbapenems. In short, these are useful tests of limited scope. For tests of β-lactam antibiotics, a more comprehensive test is needed to detect the activities of all β-lactamases against all β-lactam antibiotics.

Disk diffusion tests can be modified by a pre-incubation procedure to determine the ability of β-lactamases from *Staphylococcus aureus* to inactivate β-lactam antibiotics. Lacey, R. W., and A. Stokes, J Clin Pathol. 30:35-9 (1977). This procedure results in smaller inhibition zones than those for which the interpretive criteria of the tests were calibrated. The preincubation procedure thereby invalidates the interpretive tables that are necessary to determine antibiotic susceptibility or resistance. This is a serious deficiency because it would be unethical to base therapy on this procedure which lacks validated interpretive criteria.

The clover leaf test [Andremont, A., et al., Proceedings Reunion Interdisciplinaire de Chimiotherapie Antiinfectieuse. Societe francaise de Microbiologie, Paris:50 (1982); Kjellander, J., et al., Acta Pathologica Microbiologica Scandinavica. 61:494 (1964)] is a special technique used to detect β-lactamases and is also claimed to detect two other types of antibiotic-inactivating enzymes, chloramphenicol acetyltransferase and erythromycin esterase. This test is not an antibiotic susceptibility test and must be set up as an additional procedure. This is inconvenient and therefore a disadvantage. Furthermore there are doubts about the validity of results obtained with this procedure. Jorgensen, P. E., Chemotherapy. 31:95-101 (1985); Reig, M., et al., European journal of Clinical Microbiology. 3:561-562 (1984).

The cefoxitin induction test [Sanders, C. C., and W. E. Sanders, Jr., A.A.C. 15:792-797 (1979)] is a special procedure for detecting a particular type of bacterial β-lactamase, the inducible AmpC β-lactamase of Bush Group 1. Bush, K., et al., A.A.C. 39:1211-1233 (1995). This test does not detect all types of β-lactamases, and like the clover leaf test it is a special procedure that can be used to supplement antibiotic susceptibility tests. It is not, in itself, an antibiotic susceptibility test.

The double disk potentiation test (and its derivatives) involves strategically placing an amoxicillin/clavulanate or ticarcillin/clavulanate disk 20 to 30 mm from disks containing cefotaxime, ceftriaxone, ceflizoxime, ceftazidime, cefepime or aztreonam on an agar plate. It is therefore possible to determine if a strain of Enterobacteriaceae produces a special type of β-lactamase known as an extended-spectrum β-lactamase. Brun-Buisson, C., et al., Lancet. ii:302-306 (1987). The test is based on the ability of the β-lactamase inhibitor, clavulanate, to inhibit the extended-spectrum β-lactamase and prevent it from inactivating the cephalosporin or aztreonam antibiotics in the test. This is a special procedure, not a routine antibiotic susceptibility test, and detects only certain types of β-lactamases. It is therefore inconvenient and limited in scope.

A variety of disk and dilution tests have been derived from the principle of the double risk test. Brown, D. F., et al., J. Antimicrob. Chemother. 46:327-8 (2000); Cormican, M., G., et al., JCM. 34:1880-1884 (1996); Ho, P. L., et al., JAC. 42:49-54 (1998); Moland, E. S., et al., JCM. 36:2575-9 (1998); Sanders, C. C., et al., JCM. 34:2997-3001 (1996); Schooneveldt, J. M., et al., Pathology. 30:164-8 (1998); Thomson, K. S., et al., Antimicrob. Agents Chemother. 43:1393-400 (1999). That is, they use the ability of a β-lactamase inhibitor to inhibit an extended-spectrum β-lactamase to detect this type of β-lactamase.

The 3-dimensional test [Thomson, K. S., et al., J. Antimicrob. Chemother. 13:45-54 (1984); Thomson, K. S., and C. C. Sanders, A.A.C. 36:1877-1882 (1992); U.S. Pat. No. 5,466,583] is an approach that partially fulfills the need for improved antibiotic susceptibility testing.

In performing the direct form of the 3-dimensional test a standard quantity of the causative microorganism is uniformly spread over the surface of an agar plate in the usual manner for performing a disk diffusion test. However, before placing the antibiotic disks onto the surface of the agar, the 3-dimensional inoculation is performed. This is effected by using a sterile scalpel to cut a slit in the agar 3 mm to one side of where the antibiotic disks will be placed. A dense liquid inoculum of the test microorganism is then dispensed into the slit, the antibiotic disks are placed on the agar 3 mm from the slit, and the test is incubated.

After incubation the inhibition zones are measured by standard procedures to determine the susceptibility or resistance of the microorganism to the test antibiotics according to the interpretive criteria of the disk diffusion test. However, in addition to this, enzymatic inactivation of the antibiotics can be detected by inspecting the intersections of the 3-dimensional inoculum with the margins of the inhibition zones. Antibiotic inactivation results in a distortion or discontinuity in the usually circular inhibition zone. (These distortions or discontinuities are hereafter referred to as "3-dimensional effects".)

The 3-dimensional test thus allows the laboratory to report to the clinician not only the susceptibility or resistance of a microorganism to antibiotics, but also the ability of the microorganism to inactivate the antibiotics. As a hypothetical example, whereas a conventional antibiotic susceptibility test might indicate that a microorganism was susceptible to the two antibiotics, cefaclor and cefoxitin, the 3-dimensional test might provide additional information to show that the microorganism produced an enzyme capable of inactivating cefaclor but not cefoxitin. Thus, although the conventional test indicated that both antibiotics appeared to be equally efficacious, it would appear, from the additional information provided by the 3-dimensional test, that only cefoxitin might not be inactivated in the patient and therefore would constitute a more effective treatment than cefaclor. In this example, the information provided by the 3-dimensional test could assist a clinician to make a better choice of therapy.

In addition to the direct form of the 3-dimensional test, the indirect form is used for testing microorganisms when inhibition zones are small or absent, or as a research or diagnostic method. The indirect test is performed by inoculating the surface of the agar with a fully susceptible assay strain such as *Escherichia coli* ATCC 25922. After this, the 3-dimensional slit is cut in the agar and inoculated with a suspension of the test microorganism. Although the indirect test precludes the simultaneous determination of antibiotic susceptibilities, it permits investigation of the antibiotic inactivating enzymes of microorganisms for which the inhibition zones are too small to yield 3-dimensional results when the test is performed in the direct form of the test.

There are several problems with the 3-dimensional test. These problems include the following:

a. The procedure for making the slit in the agar for the 3-dimensional test is inconvenient and technically difficult to perform correctly.

b. Making the slit is potentially dangerous to laboratory staff because a scalpel blade contaminated with pathogenic bacteria is an infection hazard.

c. It is also technically difficult to accurately deliver the liquid 3-dimensional inoculum into the slit without overfilling the slit and possibly invalidating the test.

A variety of chemicals have been reported to disrupt or permeabilize microbial membranes, thereby increasing their permeability and causing loss of cellular contents. These include certain antibiotics, detergents, chelating agents, polycations, hydrophobic dyes, and enzymes. Nikaido, H., and M. Vaara, Microbiol Rev. 49:1-32 (1985); Piers, K. L., et al., Antimicrob. Agents Chemother. 38:2311-2316 (1994). These chemicals are often bacteriostatic and/or bacteriocidal in normal use.

BRIEF SUMMARY OF THE INVENTION

In one aspect, the present invention provides a method of determining the antibiotic susceptibility of a microorganism comprising the following steps. First, a culture of the microorganism whose susceptibility is to be determined is admixed with an antibiotic to which susceptibility is to be assayed, and a permeabilizing agent for the microorganism present in a non-growth-inhibiting microorganism-permeabilizing effective amount to form an assay culture. Next, the assay culture is incubated under appropriate culture conditions and for a time sufficient to determine the susceptibility of the microorganism to the antibiotic.

Preferably, the permeabilizing agent is dissolved or dispersed in a carrier. The carrier can be a solid carrier. A preferred solid carrier is a paper disk. Alternatively, the carrier can be a liquid carrier.

In one embodiment, the permeabilizing agent is a buffer solution. A preferred buffer solution is Tris/EDTA.

In another embodiment, the culture is provided on a solid growth medium. Alternatively, the culture is provided in a liquid growth medium.

In a further embodiment, the carrier is a solid carrier, the culture is provided on a solid growth medium, the antibiotic is provided on a solid support, and the admixing is done by contacting the culture with the solid carrier and the antibiotic provided on a solid support.

In another aspect, the present invention provides an improved method for antibiotic susceptibility testing of a microorganism in a culture by admixing the culture with an antibiotic to which susceptibility is to be assayed, and incubating the culture for a time sufficient to determine the susceptibility of the microorganism to the antibiotic, the improvement comprising admixing the culture with a permeabilizing agent for the microorganism present in a non-growth inhibiting microorganism-permeabilizing effective amount.

Preferably, the permeabilizing agent is a buffer solution. A preferred buffer solution is Tris/EDTA.

In one embodiment, the permeabilizing agent is dissolved or dispersed in a carrier. The carrier can be a solid carrier. A preferred solid carrier is a paper disk. Alternatively, the carrier can be a liquid carrier.

DETAILED DESCRIPTION OF PREFERRED EMBODIMENT

Figure 1:
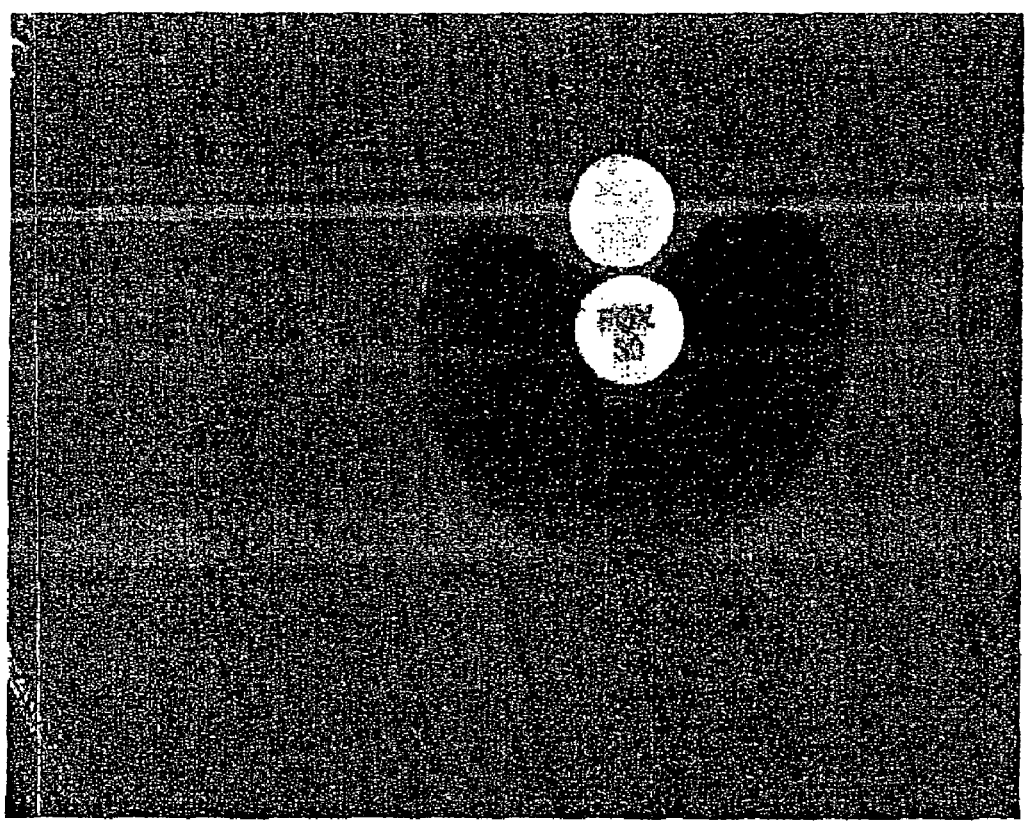
FIG. 1 shows a close up of a zone of distortion surrounding a cefoxitin disk.

The invention provides a novel method of determining the antibiotic susceptibility of a microorganism based upon increasing the permeability of the cell wall and/or cell membrane(s) of a microorganism by incubating a microorganism in the presence of a permeabilizing agent. This permeabilizing agent is preferably present in an amount that neither kills the microorganism nor significantly inhibits its ability to replicate, but nevertheless permeabilizes the microorganism. While not wishing to be bound by theory, it is believed that the presence of an appropriate concentration of permeabilizing agent permits the enhanced liberation or release of antibiotic-inactivating factors (e.g., enzymes) from the microorganism. The liberation or release of such antibiotic-inactivating factors permits a microorganism to grow in the presence of the antimicrobial agent that is inactivated by the released factors.

In another aspect, the invention provides a novel method of determining the presence of antibiotic-inactivating factors, such as antibiotic-inactivating enzymes, comprising the following steps. First, a culture of the microorganism which is suspected of producing or liberating antibiotic-inactivating factors is admixed with an antibiotic to which the antibiotic-inactivating factors are capable of inactivation, and a permeabilizing agent for the microorganism present in a non-growth-inhibiting microorganism-permeabilizing effective amount to form an assay culture. Next, the assay culture is incubated under appropriate culture conditions and for a time sufficient to determine the presence of antibiotic-inactivating factors produced or liberated by the microorganism capable of inactivating the antibiotic.

It has been found that a permeabilizing agent can be used to detect antibiotic-resistant microorganisms that would otherwise register as falsely sensitive to a test antibiotic, by facilitating the liberation or release of antibiotic-inactivating factors. Surprisingly, the microorganism can grow in the presence of a permeabilizing agent that is normally lethal to a microorganism, or inhibits the growth of a microorganism.

In one aspect, the invention comprises the use of a permeabilizing agent, in a non-growth-inhibiting, microorganism-permeabilizing effective amount. As set forth in more detail elsewhere herein, determining a non-growth-inhibiting amount of a permeabilizing agent is a matter of routine experimentation involving the titration of the permeabilizing agent for its ability to significantly inhibit microorganism growth. Similar, the determination of a microorganism-permeabilizing effective amount of a permeabilizing agent is a matter of routine experimentation involving the titration of the permeabilizing agent for its ability to permeabilize a microorganism, such as by liberation of antibiotic-inactivating factors from a known antibiotic-resistant strain of a test microorganism.

The permeabilizing agent, in the amount set forth herein, is admixed with a culture of a microorganism whose susceptibility to an antibiotic is to be determined. Alternatively, the admixture is made to determine the micoorganism's capacity to generate or liberate one or more antibiotic-inactivating factors. The culture is prepared according to methods that are well known in the art, such as by introducing an inoculum of the microorganism (such as from a clinical sample) into an appropriate growth medium. The growth medium can be a liquid growth medium, such as Luria or Meuller-Hinton broths, or a sold growth medium, such as an agar plate supplemented with necessary nutrients, such as a Mueller-Hinton agar plate.

Once the culture is prepared, the microorganism is admixed with one or more antibiotics (antimicrobial agents) to be assayed. In the case of assaying the microorganism for its ability to make or excrete an antibiotic-inactivating factor, the presence of the antibiotic is required both to provide a control for the assay, and to facilitate the production or liberation of the inactivating factor itself. The antibiotic can be needed to initiate or enhance the production of the antibiotic-inactivating factor by the microorganism. In the absence of the antibiotic, the microorganism does not necessarily need to make, maintain, sequester, or liberate the antibiotic-inactivating factor.

Antibiotic-susceptibility assays are set forth elsewhere herein, and are not meant to be limiting with respect to such assays that can be adapted for use in the instant invention. The culture is also admixed with the permeabilizing agent.

If needed, a control culture, without either antibiotic or permeabilizing agent, or both, can be prepared under similar conditions. Where the admixture is done with a liquid growth medium and a permeabilizing agent in a liquid carrier, as described elsewhere herein, serial dilutions of the antibiotic to be assayed are prepared in the liquid growth medium. Parallel samples are admixed with or without the permeabilizing agent in the liquid carrier. An antibiotic that at a particular antibiotic dilution shows antimicrobial activity in the absence of permeabilizing agent, but is ineffective at that dilution in the presence of permeabilizing agent, would be considered ineffective against the assayed microorganism, on the basis that the microorganism liberates a factor that inactivates that antibiotic.

The thus prepared culture is then incubated under appropriate culture conditions and for a time sufficient to determine the susceptibility of the microorganism to the antibiotic or antibiotics of interest. For example, an agar plate can be incubated at 35 degrees Celsius for 12 to 18 hours in an environmentally controlled incubator. A culture in a liquid medium can be incubated in a shaking water bath at 35 degrees Celsius for 12 to 18 hours on a bench top. The appropriate culture conditions and sufficient times are well known to workers of ordinary skill in the art.

As noted, the permeabilizing agent can be provided in a liquid or a solid carrier, dispersed or dissolved therein. For example, in the case of a liquid permeabilizing agent, such as a buffer solution, the buffer solution is itself in a liquid carrier. Alternatively, a detergent can be dispersed in an aqueous medium, or in growth broth, for use in the methods of the invention.

In another aspect, the permeabilizing agent is provided on a solid support. For example, the buffer solution can be impregnated onto a solid support such as a piece of filter paper. The filter paper is then left to dry, and the permeabilizing agent is dispersed onto the solid carrier.

In one embodiment, the impregnated disk is used in an antibiotic sensitivity assay to permeabilize the microorganism whose antibiotic sensitivity is being measured, without killing or significantly inhibiting the growth of the microorganism. An appropriate amount (concentration) of a permeabilizing agent to be used in preparing these impregnated disks can be determined to effectuate liberation of antibiotic-inactivating factor(s) from a microorganism, without killing or inhibiting the growth of a microorganism.

The invention is designed to increase the amount of information provided by laboratory tests in which the susceptibility of microorganisms to antimicrobial agents (sometimes referred to herein as antibiotics) is evaluated by disk diffusion methods or by other antibiotic-sensitivity determining methods. The invention provides a means to routinely detect the ability of microorganisms to inactivate antibiotics. The information can be useful in selecting appropriate antiinfective therapies for the treatment of infections, in providing epidemiological information about microorganisms, in antibiotic research, and in other fields of biological research such as genetics and enzymology.

In a preferred embodiment, the invention comprises providing a filter paper disk impregnated with an agent such as a chemical that will facilitate the release of antibiotic inactivating enzymes from bacteria or other microorganisms. This filter paper disk impregnated with the chemical is sometimes referred to herein as the reagent disk. Typically the agent in the reagent disk will be a permeabilizing agent that will disrupt the outer membrane, or both the outer and cytoplasmic membranes of a microorganism such as a bacterium to release antibiotic-inactivating enzymes from within the microorganism. In a preferred method of the invention, a disk impregnated with a permeabilizing agent is provided.

A suitable growth-medium-containing agar plate is inoculated with a lawn of test microorganism (e.g., a clinical sample, or a strain of bacteria for which antibiotic sensitivity is to be determined). An antibiotic-impregnated disk is placed onto the lawn of microorganism. The test microorganism is additionally inoculated onto a provided reagent disk, and that reagent disk is placed on the agar adjacent to, but not in contact with, an antibiotic disk of interest. The agar plate is then incubated according to methods well known in the art. After incubation, the results are interpreted as follows. Enzymatic inactivation of an antibiotic can be detected by inspecting the margin of the inhibition zone in the vicinity of the reagent disk. Antibiotic inactivation results in a distortion in the usually circular zone of inhibition. The presence of this distortion indicates that the test microorganism is capable of producing antibiotic-inactivating factors. From a clinical perspective, the use of an antibiotic that exhibits a zone of distortion would be contraindicated for treatment of an infection with the test microorganism.

It should be understood that while a preferred embodiment of the invention is as described above, the invention is not limited to that embodiment. Other solid carriers other than a filter paper disk, such as filter paper strips, pieces of nitrocellulose, or other carriers could be used as vehicles to effect contact between the microorganism and the reagent. Test methodologies other than the disk diffusion test, such as the E test [Brown, D. F. J., and L. Brown, J. Antimicrob. Chemother. 27:185-190 (1991)], or the dilution methods can also be modified for detection of antibiotic inactivating enzymes without departing from the spirit and scope of the invention.

In another aspect, the invention provides an improved method for antibiotic testing of a microorganism in a culture, as exemplified by the antibiotic susceptibility testing assays discussed elsewhere herein. The improvement comprises admixing the culture with a permeabilizing agent of the invention, in an amount that does not significantly inhibit the growth of the culture but is effective in permeabilizing the microorganisms.

In a further embodiment, the invention comprises an indirect form for testing microorganisms when inhibition zones are small or absent, or as a research or diagnostic method. The indirect form of test is performed by inoculating the surface of the agar with a fully antibiotic-susceptible assay strain such as Escherichia coli ATCC 25922. After this, the provided reagent disk is inoculated with a suspension of the test microorganism (e.g., a clinical isolate) and the test performed as described above except that the assay strain will grow on the surface of the agar instead of the causative organism. Although the indirect form of a method of the invention can preclude the simultaneous determination of antibiotic susceptibilities, it permits investigation of the antibiotic inactivating enzymes of microorganisms for which the inhibition zones are too small to yield results when the test is performed in the direct form of the test.

Exemplary permeabilizing agents useful in the present invention include those agents that increase the permeability of the cell wall and/or cell membrane(s) of a microorganism, but that are present in amounts or concentrations that will not significantly inhibit the growth or reproduction of the assayed microorganism. As is well known to those of ordinary skill in the art, not all microorganisms possess both a cell wall and a cell membrane; moreover, those microorganisms that possess both a cell wall and a cell membrane do not have walls or membranes that are structurally identical. For example, bacteria are broadly categorized as Gram-positive or Gram-negative based upon their cell wall/cell membrane structure. A permeabilizing agent useful in the present invention preferably permeabilizes the cell surface structure (cell wall or cell membrane, or both) such that antibiotic-inactivating factors are liberated from the cell. However, it is also preferred that the permeabilizing agent not kill or significantly inhibit the growth of the microorganism.

Specific exemplary permeabilizing agents include the following:

Inorganic salts, such as sodium chloride (NaCl), magnesium chloride ($Mg_2Cl$), potassium chloride (KCl) and the like;

Quaternary ammonium compounds such as benzalkonium chloride (BAC), cetylpyridium chloride, 3-(trimethoxysilyl)propyldimethyloctadecyl ammonium chloride and the like;

Buffer solutions, such as Tris/EDTA (TE) buffer, NaCl/Tris/EDTA (STE) buffer, glucose/Tris/EDTA (GTE) buffer, and the like;

Hypotonic or hypertonic agents, such as sugar solutions, including glucose, dextrose, sucrose, fructose, lactose and the like;

Antibiotics such as Piperacillin, Aztreonam, Amdinocillin, Ceftazidime, Polymyxin B, Polymyxin B nonapeptide, or Gentamicin, and the like;

Commercially available detergent or surfactant-containing agents such as Blind Brite™, Maxaquin™, HyVee Glass Cleaner™, Life Tree™, Rave™, Dawn™, and the like;

Other commercially available materials such as Isoclean™ concentrate, Sight Savers™ lens cleaner, Wash™ (green handwash), Micro Lab Cleaning Solution™, Jet Clean™ test tube cleaner, Limonene™, and the like;

Other surfactants and/or detergents such as TritonX-100™, sodium dodecyl sulfate (SDS), SDS (5%) mixed with acetone, Sarcosyl™, Sarcosyl™ mixed with acetone, Tween™ (polysorbate) 80, Tween™ 80 mixed with acetone, Tween™ 85, Brij™ 56, polyethylene glycol, polypropylene glycol, dansyl-polymyxin and the like.

Other exemplary permeabilizing agents include CHAPS (3-[(3-Cholamidopropyl)dimethylammonio]-1-propanesulfonate) electrophoresis reagent, $\leqq 10$ mM (Sigma cat # C-9426), lactic acid, and sodium hexametaphosphate (sodium polyphosphate) (chelating agent).

Natural peptide agents such as cecropins (cationic peptides), melittin (cationic peptide), bactenecin, magainins (frog host defense peptides), tachyplesins (cationic peptides), polyphemusins (cationic peptides), and synthetic peptides and the like can also be used as preferred permeabilizing agents.

A preferred permeabilizing agent is Tris/EDTA (TE) buffer, commercially available from Sigma-Aldrich (catalog number T-9285). As supplied, the TE buffer is at a 100× concentration, comprised of 1.0 molar Tris-HCl (pH approximately 8.0) and 0.1 molar EDTA. The TE buffer is preferably placed onto a disk at a concentration of 100 millimolar, 200 millimolar, 0.5 molar, 1 molar, 2 molar or 10 molar. The TE buffer is further preferably placed onto a disk at a concentration of 100×, 50×, 25× and 10×. Methods for determining the optimal concentration of a particular permeabilizing agent are given elsewhere herein.

As noted elsewhere herein, a permeabilizing agent preferably permits or facilities the release of antibiotic-inactivating factors from within a microorganism while not significantly inhibiting the growth of that microorganism. The ability of a permeabilizing agent to liberate or release antibiotic-inactivating factor(s) from a microorganism can be determined by, for example, quantitation of the amount of antibiotic inactivating factor, such as an enzyme, released. Such quantitation can be determined by, for example, spectrophotometric hydrolysis assays using either nitrocefin or cefaclor as substrates. The ability of a permeabilizing agent to liberate or release antibiotic-inactivating factor(s) from a microorganism can also be determined by, for example, using the methods of the present invention, or using other antibiotic-sensitivity tests such as the 3-dimensional test discussed elsewhere herein. Exemplary determinations of the ability of a permeabilizing agent to liberate or release antibiotic-inactivating factor(s) from a microorganism are described in the Examples set forth elsewhere herein.

A preferred permeabilizing agent also does not significantly inhibit the growth of a microorganism. This property of a preferred permeabilizing agent can be determined by, for example, applying varying concentrations of a particular permeabilizing agent to lawn cultures of a variety of microorganisms to determine if inhibition of growth of the lawn culture occurred. Alternatively, the growth rates of various microorganisms in the presence of varying concentrations of a permeabilizing agent can also be determined, using techniques well known in the art. Exemplary determinations of the ability of a permeabilizing agent to permit the growth of a microorganism are described in the Examples set forth elsewhere herein.

In another embodiment, the present invention comprises a kit comprising a permeabilizing agent-impregnated disk and instructions for performing an antibiotic sensitivity test to detect microorganisms that liberate antibiotic-inactivating factors. In a preferred embodiment, the permeabilizing agent is Tris/EDTA buffer.

As can be readily seen, the invention provides novel benefits and advantages over other antibiotic-sensitivity testing methods. The invention permits antibiotic-sensitivity testing to be performed, for example, on the surface of the agar, rather than the technically challenging aspect of some other methods that require the insertion of bacterial inoculum into a slit in the agar. Furthermore, the invention discloses the use of a permeabilizing agent that facilitates the release of antibiotic inactivating factors from microorganisms, without significantly inhibiting the growth of those microorganisms. Current antibiotic susceptibility testing techniques cannot enhance the release of such factors, leading to the possibility of false-positive results. Therefore, current antibiotic susceptibility testing techniques can lead a clinician to believe that a particular microorganism is sensitive to an antibiotic based on these in vitro results, only to find empirically that the antibiotic is ineffectual in vivo. The present invention provides more robust in vitro information that can detect microorganisms that are likely to be resistant to a particular antibiotic in vivo.

EXAMPLES

Example 1

Determination of Release of Antibiotic-Inactivating Factors

In this Example, *E. coli* MISC 208 (which produces the extended spectrum β-lactamase SHV-2) was used as a test organism and nitrocefin was the substrate in spectrophotometric hydrolysis assays. The *E. coli* strain was harvested directly into 100 microliters of Mueller Hinton Broth and mixed with 100 microliters of the permeabilizing agent.

In the hydrolysis assay, units of activity are calculated as:

$$\text{Units} = \frac{\text{Change in optical density } (OD)/\text{minute} \times 10}{\text{Extinction coefficient}}$$

The hydrolysis assay was performed essentially as described by O'Callaghan, C. H., et al., A.A.C. 1:283-288 (1972). Briefly, a 100 µM solution of nitrocefin was used as a substrate. The nitrocefin was prewarmed to 37° C. The hydrolysis assay was performed at 37° C. at a wavelength of 389.5 with an extinction coefficient of −0.024. An appropriate cuvette was filled with 0.9 ml of the prewarmed nitrocefin substrate and 100ul of permeabilized bacterial suspension was added. The contents of the cuvette were immediately mixed by inversion and the cuvette was placed in a spectrophotometer. Absorbance was assayed at 5-second intervals for up to 5 minutes with the 37° C. temperature maintained by means of a circulating water bath that warmed the cuvette block. When the assay was complete, the activity was calculated according to the above formula.

| Permeabilizing Agent | Units of β-lactamase Activity (Nitrocefin as substrate) |
|---|---|
| TE/Room temp | 47 |
| TE/0° C. | 102 |
| Tris/0° C. | 41 |
| Water (control) | 0 |

Example 2

Determination of Release of Antibiotic-Inactivating Factors

The experiment in Example 1 was repeated using *E. coli* MISC 208 and cefaclor as substrate in the hydrolysis assays.

| Permeabilizing Agent Preparation | Units of β-lactamase Activity (Cefaclor as substrate) |
|---|---|
| Benzalkonium chloride 200 µg/ml | 16 |
| Polymyxin B 10 µg/ml | 3.8 |
| Polymyxin B 30 µg/ml | 15 |
| TE | 79 |

Example 3

Determination of Release of Antibiotic-Inactivating Factors

The experiment in Example 1 was repeated using *E. coli* V1104 to evaluate a variety of permeabilizing agents. Nitrocefan was the hydrolysis substrate.

| Permeabilizing Agent Preparation | Units of β-lactamase Activity (Nitrocefin as substrate) |
|---|---|
| Aztreonam | 210 |
| No reagent/0° C. | 214 |
| No reagent/45° C. | 0 |
| Ceftazidime | 196 |
| Piperacillin | 202 |

Other exemplary microorganisms that can be used in the determination of release of antibiotic-inactivating factors include those in the following Table.

| Strain | Enzyme | Units (vs nitrocefin) |
|---|---|---|
| *E. coli* V1104 | | 202 |
| *E. coli* 165* | pI 5.95 TEM ESBL | 43 |
| MG32 | TEM-1 + TEM-12 | 349 |
| *K. pneumoniae* V1102 | | 227 |

Example 4

Determination of Lack of Significant Growth Inhibition

A variety of test strains have been harvested directly into 100 microliters of Mueller Hinton Broth and mixed with 100 microliters of each permeabilizing agent of interest. Then 20 microliters of each of these mixtures was applied to blank filter paper disks, and the disks transferred to freshly inoculated agar lawn cultures of a variety of test microorganisms and the plates were incubated overnight at 37° C. After overnight incubation, the cultures were inspected for the presence or absence of an inhibition zone around the disk. An inhibition zone inferred unsuitability of the permeabilizing agent for the test at the concentration used.

A variant of this method is to directly apply the reagent to a disk without previously mixing the reagent with a microorganism, and to evaluate as above.

Making the Reagent Disk

1. A solution of equal parts of physiological saline and Tris EDTA (Sigma Chemicals) is made.
2. A 20 microliter aliquot of the permeabilizing agent solution was placed onto a filter paper disk and allowed to dry.

Performing and Interpreting the Test

Figure 2:
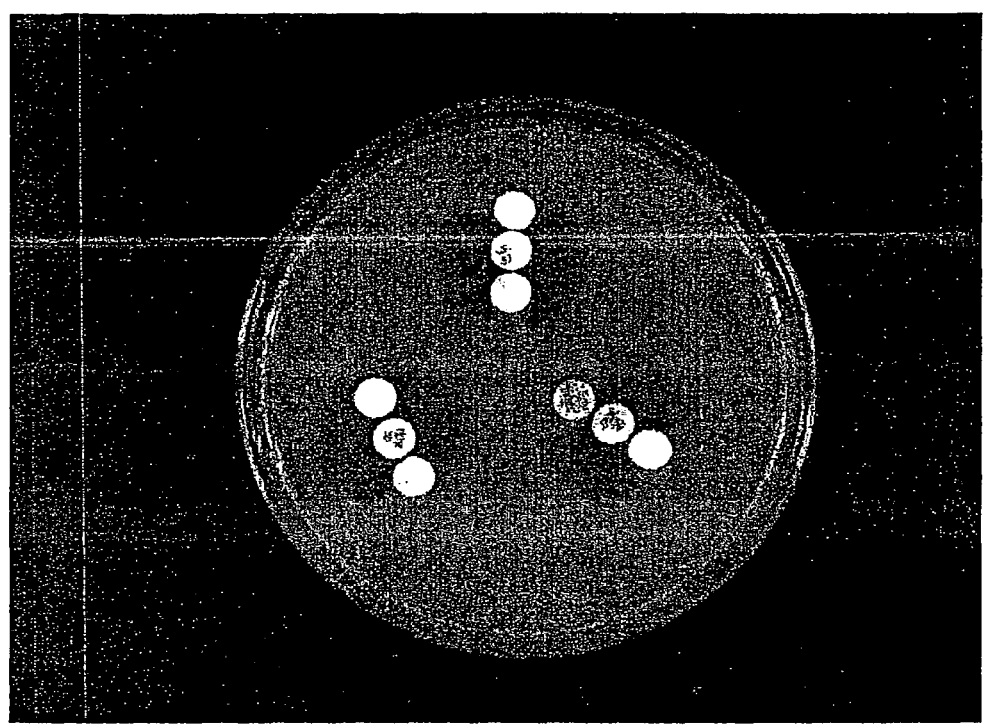
FIG. 2 shows one embodiment of the invention. Here, the indirect form of a method of the invention is shown in which five test microorganisms and a negative control organism are tested. In this assay the fully susceptible strain *E. coli* ATCC 25922 was used as the lawn culture to assay for inactivating factors produced by the test and control microorganisms. Three commercially manufactured cefoxitin disks (labeled FOX 30) are bracketed by the reagent test disks. A test or control organism was applied to each of the reagent disks prior to their placement proximal to the cefoxitin disks. Strong indentations of the inhibition zone margins indicate inactivation of cefoxitin by inactivating factors released from the test microorganisms subsequent to encountering the permeabilizing agent in the disks. The negative control has no distortion (bottom disk of top set of 3 disks with orientation pointing to 12 o'clock). A weakly positive test occurred at the disk closest to 9 o'clock (shown as slight flattening or blunting of the inhibition zone margin). This result was obtained with a strain of *Klebsiella pneumoniae* previously determined to be a low level producer of a cefoxitin-inactivating β-lactamase. (This strain is a potential candidate as a quality control strain associated with the threshold of sensitivity of detection of the test for this particular antibiotic inactivating factor).

1. The filter paper disk impregnated with the permeabilizing agent was rehydrated with 20 microliters of sterile physiological saline.
2. Using a cotton swab or loop, a test organism was rubbed onto the rehydrated disk.
3. A Mueller Hinton Agar plate was inoculated with a 0.5 McFarland of *E. coli* ATCC 25922.
4. A cefoxitin disk was placed onto the surface of the agar plate. The rehydrated disk inoculated with the test organism next was placed next to the cefoxitin disk, at a distance of about 0.5-1.0 mm.
5. The agar plate was incubated at 37° C. for about 16 hours, or overnight.
6. Distortion of the cefoxitin zone was interpreted as a positive result (i.e., the presence of an antibiotic-inactivating factor was detected), whereas lack of distortion of the cefoxitin zone was interpreted as a negative result. See FIGS. 1 and 2.

Example 5

Detection of Antibiotic-Resistant Microorganisms

This study reports its utility for investigation of *Klebsiella* isolates suspected of harboring pAmpCs.

Methods: Thirty isolates of *Klebsiella* spp. with cefoxitin MICs ≧16 micrograms per milliliter were investigated using the methods of the invention. All negative results were confirmed with the three-dimensional test, discussed elsewhere herein, and positive results were confirmed by isoelectric focusing (IEF) and inhibitor studies. A filter paper disk was impregnated with 100×TE which had been diluted with an equal volume of physiological saline. The disk was rehydrated with 20 microliters of saline and several colonies of the test isolate were inoculated onto the disk. The inoculated disk was then placed beside a cefoxitin disk (almost touching) on a Mueller-Hinton agar plate inoculated with a lawn of *E. coli* ATCC 25922. After overnight incubation, a positive test appeared as a flattening or indentation of the cefoxitin inhibition zone near the test disk. A negative test had an undistorted zone.

Results: Of the 30 isolates tested, 10 were positive and 20 were negative (also negative with the three-dimensional test). IEF and inhibitor studies of the positive isolates indicated that 9 of the 10 isolates produced β-lactamases that were inhibited by cloxacillin with pIs of either 7.2, 7.7 or ≧9.0, findings consistent with AmpC production. These enzymes were interpreted to be plasmid-mediated because *Klebsiella* lacks a chromosomal AmpC. The other positive isolate had an elevated imipenem MIC and produced a carbapenem-hydrolyzing enzyme that also hydrolyzed cefoxitin.

Materials and Methods

Isolates

Thirty recent isolates of *Klebsiella* spp. were collected from patients in United States hospitals.

Susceptibility

Antimicrobial susceptibility was determined by NCCLS microdilution methodology using an investigational Microscan dehydrated panel.

Three-dimensional Test

Figure 3:
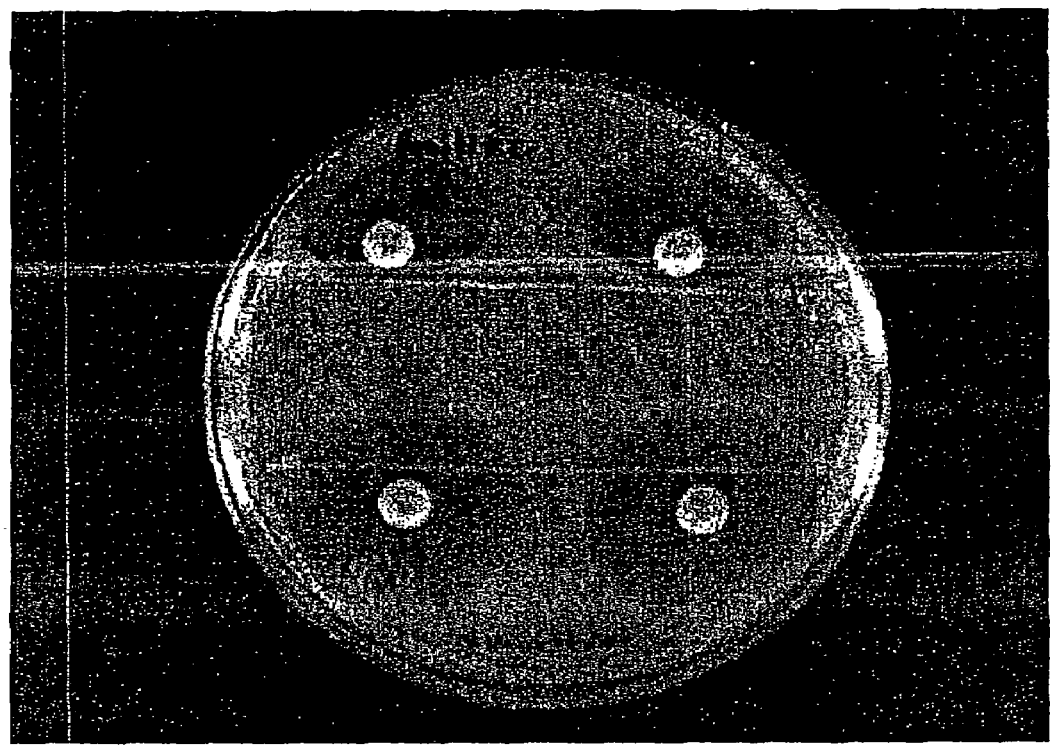
FIG. 3 shows a three-dimensional test demonstrating the enzymatic inactivation of cefoxitin by a penicillin-resistant strain of *Klebsiella*.

Enzymatic inactivation of cefoxitin was investigated by the three-dimensional method. The surface of a Mueller-Hinton agar plate was inoculated with a lawn of a standardized inoculum of *E. coli* ATCC 25922. A slit was then cut into the plate with a sterile scalpel blade. Into the slit, a suspension containing a heavy inoculum ($\geq 10^9$ CFU per milliliter) of the test organism was dispensed by capillary action from a micropipette tip. A cefoxitin disk was then placed on the agar 3 millimeters from the slit. After overnight incubation at 35° C., the plate was examined for evidence of cefoxitin inactivation, as indicated by a characteristic distortion of the inhibition zone margin. The absence of this feature indicated no significant inactivation of cefoxitin (FIG. 3).

AmpC Disk Test

Figure 4:
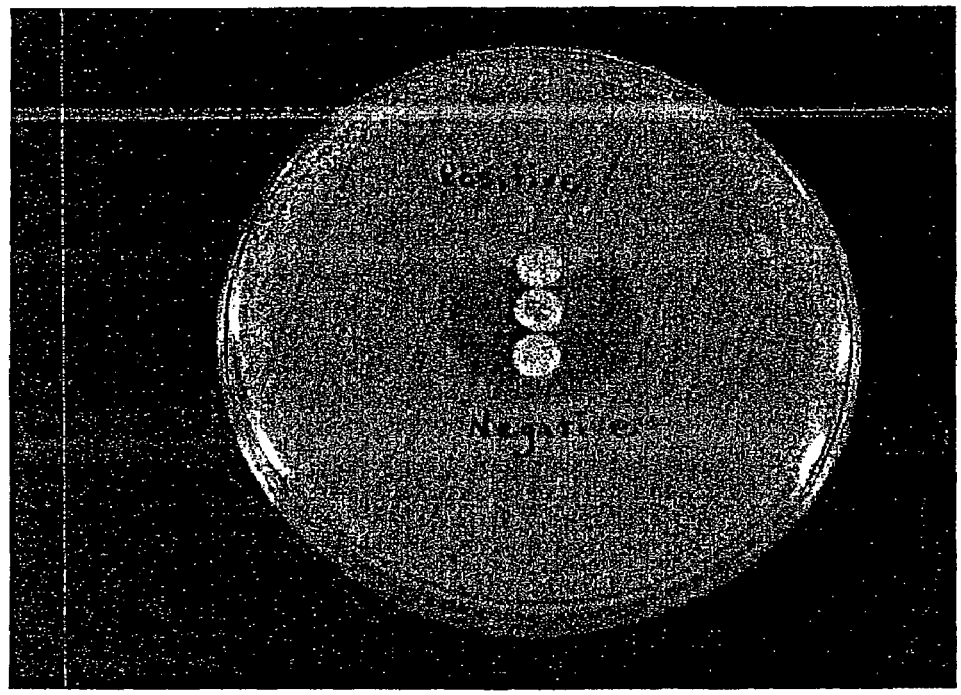
FIG. 4 shows an embodiment of the invention as described above for FIG. 2, except that only a single cefoxitin disk is shown. The portion of FIG. 4 marked "Positive" displays the distorted inhibition zone characteristic of a permeabilizing agent of the invention. The portion of FIG. 4 marked "Negative" displays the lack of distortion where a control reagent disk, not having a permeabilizing agent, is placed proximal to the antibiotic disk.

Enzymatic inactivation of cefoxitin was also investigated by a disk test that used a filter paper disk impregnated with a permeabilizing agent of the invention, TE, as described elsewhere herein. The disk was rehydrated with 20 microliters of sterile saline and then inoculated with several colonies of the test organism. The surface of a Mueller-Hinton agar plate was inoculated with a lawn of a standardized inoculum of *E. coli* ATCC 25922. The inoculated disk was then placed beside a cefoxitin disk (almost touching) on the inoculated plate. After an overnight incubation at 35 degrees Celsius, a positive test appeared as a flattening or indentation of the cefoxitin inhibition zone in the vicinity of the test disk. A negative test had an undistorted zone (FIG. 4).

Isoelectric Focusing

Crude sonicates were subjected to analytical isoelectric focusing (IEF) on an ampholine polyacrylamide gel (pH range 3.5-9.5) on a flatbed apparatus (Multiphor LKB). Inhibitor overlays of the IEF gel were performed with 1000 µM clavulanic acid and cloxacillin.

Results

Thirty *Klebsiella* spp. isolates with cefoxitin MICs $\geq 16$ µg/ml were tested with the AmpC disk test. Of these, 20 were negative and ten were positive. The negative isolates were confirmed as negative with the three-dimensional test. IEF and inhibitor studies revealed that nine of the ten positive isolates produced β-lactamases with pIs of either 7.2, 7.7, or $\geq 9.0$ that were inhibited by cloxacillin. These findings were consistent with AmpC production. These enzymes were interpreted to be plasmid-mediated because *Klebsiella* spp. lack a chromosomal AmpC. The other positive isolate had an elevated imipenem MIC (64 µg/ml) and produced a carbapenem-hydrolyzing enzyme that was also capable of hydrolyzing cefoxitin.

The foregoing description and the examples are intended as illustrative and are not to be taken as limiting. Still other variations within the spirit and scope of this invention are possible and will readily present themselves to those skilled in the art.

The invention claimed is:

1. A method of determining antibiotic susceptibility of a microorganism comprising:
    a) admixing a test microorganism whose susceptibility is to be determined with an antibiotic to which susceptibility is to be assayed, a permeabilizing agent for the test microorganism present in a non-growth-inhibiting microorganism-permeabilizing effective amount, and a strain of microorganism with known susceptibility for said antibiotic to form an assay culture;
    b) providing a control comprising the test microorganism, the antibiotic, and said strain of microorganism, without a non-growth-inhibiting microorganism-permeabilizing effective amount of a permeabilizing agent;
    c) incubating said assay culture and control under appropriate conditions and for a time sufficient to determine the susceptibility of the test microorganism to said antibiotic; and
    d) comparing growth in the assay culture to growth in the control,
    whereby, significantly more growth or a distortion in a zone of inhibition in the assay culture is indicative of resistance of the test microorganism to the antibiotic attributable to inactivation of the antibiotic.

2. The method of claim 1, wherein said permeabilizing agent is dissolved in or dispersed on a carrier.

3. The method of claim 2, wherein said carrier is a solid carrier.

4. The method of claim 3, wherein said solid carrier is a paper disk.

5. The method of claim 2, wherein said carrier is a liquid carrier.

6. The method of claim 1, wherein the permeabilizing agent is a buffer solution.

7. The method of claim 6, wherein said buffer solution is Tris/EDTA.

8. The method of claim 1, wherein the permeabilizing agent is a surfactant or detergent.

9. The method of claim 1, wherein said test microorganism and said permeabilizing agent are admixed before admixing with other components of the assay culture.

10. The method of claim 1, wherein said assay culture is provided on solid growth medium.

11. The method of claim 10, wherein said permeabilizing agent is provided on a solid carrier, said test microorganism is applied to said solid carrier, said antibiotic is provided on a solid support, said strain of microorganism is inoculated onto the solid growth medium, said admixing is by placing the solid carrier proximal said solid support on the solid growth medium, and said significant growth is observed as a distortion in a zone of inhibition in the assay culture.

12. The method of claim 1, wherein said antibiotic is a beta-lactam-containing antibiotic.

13. The method of claim 12, wherein said beta-lactam-containing antibiotic is a cefoxitin.

14. The method of claim 12, wherein said beta-lactam-containing antibiotic is a carbapenem.

15. The method of claim 12 wherein said beta-lactam-containing antibiotic is an imipenem.

16. The method of claim 1, wherein said assay culture is provided in liquid growth medium.

17. The method of claim 1, further comprising: detecting an antibiotic-inactivating factor produced by the test microorganism based on the growth in the assay culture and control, whereby, significantly more growth or a distortion in a zone of inhibition in the assay culture is indicative of production of an antibiotic-inactivating factor by the test microorganism.

18. The method of claim 17, wherein said antibiotic-inactivating factor is a beta-lactamase.

19. The method of claim 18, wherein said beta-lactamase is an AmpC.

20. The method of claim 18, wherein said beta-lactamase is a carbapenemase.

21. A method of determining antibiotic susceptibility of a microorganism comprising:
   a) admixing a test microorganism whose susceptibility is to be determined with an antibiotic to which susceptibility is to be assayed, a permeabilizing agent for the test microorganism present in a non-growth-inhibiting microorganism-permeabilizing effective amount, and a strain of microorganism with known susceptibility for said antibiotic to form an assay culture;
   b) incubating said assay culture under appropriate conditions and for a time sufficient to determine the susceptibility of the test microorganism to said antibiotic; and
   c) detecting growth in the assay culture,
   whereby, growth in the assay culture is indicative of resistance of the test microorganism to the antibiotic.

22. The method of claim 21, wherein said permeabilizing agent is dissolved in or dispersed on a carrier.

23. The method of claim 22, wherein said carrier is a solid carrier.

24. The method of claim 23, wherein said solid carrier is a paper disk.

25. The method of claim 22, wherein said carrier is a liquid carrier.

26. The method of claim 21, wherein the permeabilizing agent is a buffer solution.

27. The method of claim 26, wherein said buffer solution is Tris/EDTA.

28. The method of claim 21, wherein the permeabilizing agent is a surfactant or detergent.

29. The method of claim 21, wherein said test microorganism and said permeabilizing agent are admixed before admixing with other components of the assay culture.

30. The method of claim 21, wherein said assay culture is provided on solid growth medium.

31. The method of claim 30, wherein said permeabilizing agent is provided on a solid carrier, said test microorganism is applied to said solid carrier, said antibiotic is provided on a solid support, said strain of microorganism is inoculated onto the solid growth medium; said admixing is by placing the solid carrier proximal said solid support on the solid growth medium, and said growth is observed as a distortion in a zone of inhibition in the assay culture.

32. The method of claim 21, wherein said antibiotic is a beta-lactam-containing antibiotic.

33. The method of claim 32, wherein said beta-lactam-containing antibiotic is a cefoxitin.

34. The method of claim 32, wherein said beta-lactam-containing antibiotic is a carbapenem.

35. The method of claim 32, wherein said beta-lactam-containing antibiotic is an imipenem.

36. The method of claim 21, wherein said assay culture is provided in liquid growth medium.

37. The method of claim 21, further comprising: detecting an antibiotic-inactivating factor produced by the microorganism based on the growth in the assay culture, wherein significant growth of the strain of microorganism or a distortion in a zone of inhibition in the assay culture is indicative of production of an antibiotic-inactivating factor by the test microorganism.

38. The method of claim 37, wherein said antibiotic-inactivating factor is a beta lactamase.

39. The method of claim 38, wherein said beta-lactamase is an AmpC.

40. The method of claim 38, wherein said beta-lactamase is a carbapenemase.

* * * * *